United States Patent [19]

Saran

[11] Patent Number: 4,760,208

[45] Date of Patent: Jul. 26, 1988

[54] PROCESS FOR COUPLING TELOMERS OF CHLOROTRIFLUOROETHYLENE

[75] Inventor: Mohan S. Saran, Grand Island, N.Y.

[73] Assignee: Occidental Chemical Corporation, Niagara Falls, N.Y.

[21] Appl. No.: 502,885

[22] Filed: Jun. 9, 1983

[51] Int. Cl.$^4$ .................. C07C 17/04; C07C 17/26; C07C 19/00; C07C 21/18

[52] U.S. Cl. ............................ 570/153; 570/135; 570/134; 570/175

[58] Field of Search ............... 570/172, 171, 175, 138, 570/139, 156, 134, 135, 15 J

[56] References Cited

U.S. PATENT DOCUMENTS

| | | | |
|---|---|---|---|
| 2,705,229 | 3/1955 | Davis et al. | 570/138 |
| 2,739,960 | 3/1956 | Dittman | 570/156 |
| 2,788,375 | 4/1957 | Ehrenfeld | 570/138 |
| 2,875,253 | 2/1959 | Barnhart | 570/139 |
| 3,046,304 | 7/1962 | Haszeldine | 570/134 |
| 3,308,175 | 3/1967 | Barr | 570/172 |
| 3,843,734 | 10/1974 | Trebillon | 570/139 |

FOREIGN PATENT DOCUMENTS

| | | | |
|---|---|---|---|
| 542435 | 6/1957 | Canada | 570/156 |
| 761053 | 11/1956 | United Kingdom | 570/138 |

*Primary Examiner*—J. E. Evans
*Attorney, Agent, or Firm*—James F. Tao; William G. Gosz

[57] ABSTRACT

A process for coupling two low molecular weight telomers of chlorotrifluoroethylene comprises reacting the telomers in a solvent with an amount of iron sufficient to form a coupled olefin. The olefin can then be fluorinated using a suitable fluorinating agent, such as chlorine trifluoride, to form a saturated product. Preferably, the solvent for the coupling reaction is acetonitrile, and the reaction is conducted under reflux conditions. A small amount of $FeCl_2$ can optionally be added to the reaction mixture as an initiator for the reaction.

7 Claims, No Drawings

PROCESS FOR COUPLING TELOMERS OF CHLOROTRIFLUOROETHYLENE

BACKGROUND OF THE INVENTION

The present invention relates to a process for coupling low molecular weight telomers of chlorotrifluoroethylene, hereinafter designated as "CTFE", to produce commercially useful products.

CTFE telomers are saturated, low molecular weight polymers, typically of general formula $CCl_3(CF_2CClF)_nCl$, where n, the molecular number or chain length (the number of repeating units in the telomer chain) is in the range of 1 to 20.

Various methods of preparing such CTFE telomers are known in the prior art and have been practiced commercially for many years. An article by William T. Miller, Jr. et al in *Industrial and Engineering Chemistry*, pages 333–337 (1947), entitled "Low Polymers of Chlorotrifluoroethylene", describes a process for producing low molecular weight polymers of CTFE by carrying out the polymerization in a solution of chloroform using benzoyl peroxides as a polymerization promoter. Other solvents disclosed in the reference as being useful for this purpose include carbon tetrachloride and tetrachloroethylene. The solution is heated in a pressure vessel for 1¾ hours at 100° C., and the unreacted CTFE monomer and chloroform are removed by distillation, leaving a "crude" telomer of general formula $CHCl_2(CF_2CClF)_nCl$, which can be further heated and distilled to yield products ranging from a light oil to a semi-solid wax or grease.

Another process which has been developed for producing low molecular weight CTFE polymers is described in U.S. Pat. No. 2,788,375, issued Apr. 9, 1957. This process comprises reacting CTFE with a saturated organic bromo compound, such as bromotrichloromethane, in the presence of actinic light in a deoxygenated system to obtain saturated bromopolychlorofluoro compounds containing one or more CTFE units per molecule. These saturated bromopolychlorofluoro compounds can then be converted to corresponding polychlorofluoro compounds by reaction with chlorine, and subsequently reacted with fluorinating agents to yield more highly fluorinated products.

A more recent development in this field is described in a series of articles by Y. Peitrasanta et al entitled "Telomerization by Redox Catalysis" appearing in the *European Polymer Journal*, Vol. 12 (1976). This technology involves the reaction of a chlorinated telogen, such as carbon tetrachloride, with CTFE in the presence of benzoin and a suitable redox catalyst, such as ferric chloride hexahydrate ($FeCl_3.6H_2O$). The telomerization reaction is suitably carried out in acetonitrile which is a common solvent for the reactants and catalysts. The telomerization reaction can be illustrated as follows:

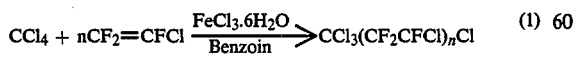

$$CCl_4 + nCF_2\!=\!CFCl \xrightarrow[\text{Benzoin}]{FeCl_3.6H_2O} CCl_3(CF_2CFCl)_nCl \quad (1)$$

Such telomers can be fluorinated with known fluorinating agents, such as cobalt trifluoride, chlorine trifluoride or hydrogen fluoride to produce products which have a higher degree of stability, and are therefore of more commercial importance. Such fluorination processes are disclosed in British Pat. Nos. 712,184 and 761,053, U.S. Pat. No. 2,636,908, and U.S. Pat. No. 2,886,607.

There are certain disadvantages inherent in all the methods used to produce CTFE telomers which are suitable for particular applications. For example, the production of hydraulic fluids or light oils typically requires telomers having molecular numbers of from about 3 to about 6, while the production of greases or waxes requires longer chain length telomers, i.e. those having molecular numbers of about 12 or more. For such applications, it is desirable to maximize the yield of products having the specific characteristics as defined by the end user's product specifications. This necessitates a fairly narrow range of molecular weights in most instances. However, commercial processes actually produce a distribution of telomers having a comparatively wide range of molecular weights, including low molecular weight telomers, i.e. those having molecular numbers of 1 and 2, which due to their volatility have no commercial value.

In U.S. Pat. No. 4,307,259, a process is described for coupling trimers which are prepared by the gas phase photochlorination of bromotrifluoroethylene. The trimers, which are obtained by fractional distillation of the polymerization products, contain a single bromine atom on a single end group of each trimer. The trimers are reacted with one mole of zinc per two moles of trimer in the presence of acetic anhydride forming $ZnBr_2$, and a coupled, fully saturated product having twelve carbon atoms.

It is therefore a principle object of this invention to provide a process for coupling low molecular weight telomers of CTFE to produce unsaturated compositions of a higher molecular weight which can be further fluorinated to yield a stabilized product. It is further the object of this invention to provide a process for utilizing the lighter weight telomers from a CTFE telomerization process to produce higher molecular weight telomers useful as hydraulic fluids.

SUMMARY OF THE INVENTION

In accordance with the present invention, there is provided a process for coupling two low molecular weight telomers of chlorotrifluoroethylene comprising reacting said telomers in a solvent with a sufficient amount of iron to form a coupled olefin. The solvent for the reaction preferably comprises acetonitrile, and the reaction is preferably carried out at a temperature in the range of from about 50° C. to about 150° C. and at about atmospheric pressure. A small amount (1%–2%) of $FeCl_2$ can be added to the reaction as an initiator for the reaction.

The olefin prepared by this process can then be fluorinated to form a stabilized, saturated telomer useful as a nonflammable hydraulic fluid. Suitable fluorinating agents include chlorine trifluoride, cobalt trifluoride, and elemental fluorine.

DESCRIPTION OF THE PREFERRED EMBODIMENTS

The coupling process of the present invention comprises the reaction of two low molecular weight telomers of chlorotrifluoroethylene in a solvent, such as acetonitrile, with a sufficient amount of iron to form a coupled olefin. Such telomers can be initially prepared using a variety of techniques. although due to overall efficiency and convenience, it is preferred to prepare such telomers by reacting carbon tetrachloride with chlorotrifluoroethylene in an acetonitrile solvent in the presence of a catalytic amount of FeCl$_3$. Such a reaction can be illustrated as follows:

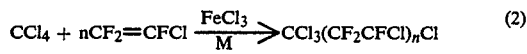

$$CCl_4 + nCF_2=CFCl \xrightarrow[M]{FeCl_3} CCl_3(CF_2CFCl)_nCl \quad (2)$$

wherein M is a metal or alloy selected from the group consisting of iron, nickel, cobalt, vanadium, molybdenum, chromium, their alloys and mixtures thereof. This process is conducted at a temperature in the range of from about 90° C. to about 150° C. and a pressure in the range of from about 150 p.s.i. to about 300 p.s.i., and is described in more detail in co-pending U.S. application Ser. No. 374,561, filed May 3, 1982 now abandoned.

In reaction (2), n designates the chain length of the telomer and will typically range from 1 to 20. However, the distribution of telomers within this range is nonuniform, with the lighter weight telomers generally comprising a disporportionately high percentage of the final product. As an example, a product distribution having from 20% to 30% of CCl$_3$(CF$_2$CFCl)Cl (wherein n=1), and 10% to 20% of CCl$_3$(CF$_2$CFCl)$_2$Cl (wherein n=2), is not unusual. Unfortunately, such lighter weight telomers are too volatile to be useful for most practical applications, such as nonflammable hydraulic fluids. According to the present invention, however, such telomers can be coupled to form heavier and more useful products by reaction with iron in acetonitrile solvent. The following reaction illustrates this coupling process for two telomers having chain lengths of 1 and 2, respectively:

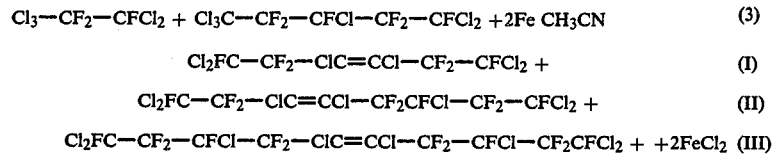

Cl$_3$—CF$_2$—CFCl$_2$ + Cl$_3$C—CF$_2$—CFCl—CF$_2$—CFCl$_2$ +2Fe CH$_3$CN     (3)

Cl$_2$FC—CF$_2$—ClC=CCl—CF$_2$—CFCl$_2$ +     (I)

Cl$_2$FC—CF$_2$—ClC=CCl—CF$_2$CFCl—CF$_2$—CFCl$_2$ +     (II)

Cl$_2$FC—CF$_2$—CFCl—CF$_2$—ClC=CCl—CF$_2$—CFCl—CF$_2$CFCl$_2$ + +2FeCl$_2$ (III)

Reaction (3) can be carried out at a temperature in the range of about 50° C. to about 150° C. and at about atmospheric pressure. Preferably, the reaction is carried out under reflux conditions. During the reaction, the iron is oxidized by the chlorine to produce two moles of ferrous chloride per mole of olefin. In effect, the iron serves to dechlorinate the telomer reactants thereby producing an unsaturated product. For this reason, it is preferred to use at least one mole of iron per mole of telomer reactant, although amounts of iron which are somewhat less than the stoichiometric amount can also be used.

A small amount of FeCl$_2$ (1%–2%) can be added to the reaction as an initiator. The addition of FeCl$_2$ to the initial reaction proceeds slowly and is excessively exothermic due to the build-up of reactants. This condition can also be minimized by a reaction sequence wherein iron is added in small amounts to a mixture of acetonitrile and telomer, or by adding the telomer to a mixture of acetonitrile and iron. Alternatively, all of the reactants can be reacted simultaneously. This latter procedure results in the generation of excessive amounts of heat which must be removed by cooling.

After the reaction is substantially complete, the acetonitrile solvent can be distilled off, using conventional techniques, accompanied by the simultaneous addition of a low boiling telomer, i.e. n=1, or an inert solvent, to maintain a suspended slurry. The product can then be filtered to separate the iron salts as a filter cake, and further distilled to separate the added telomer and product olefins.

The olefins produced according to reaction (3) can then be fluorinated to form a saturated, stabilized product. A suitable fluorinating agent for this purpose is chlorine trifluoride (ClF$_3$), although other fluorinating agents can be used. Cobalt trifluoride or ferric chloride can also be used as catalysts in combination with chlorine trifluoride. The addition of such cobalt or iron salts produces a product having slightly different characteristics and structure than the use of chlorine trifluoride alone. Such fluorination can be advantageously carried out at a temperature in the range of from about 80° C. to about 200° C.

Although the coupling reaction (3) has been described in terms of the reaction of two telomers of different chain lengths, i.e. chain lengths of 1 and 2, it should be appreciated that the process of this invention is applicable to any combination of low molecular weight CTFE telomers. For instance, the reaction of two telomers both having chain lengths of 1 produces an olefin of formula C$_6$F$_6$Cl$_6$. Accordingly, the term "low molecular weight telomer", as used in the present specification and claims, is intended to denote a CTFE telomer of general formula CCl$_3$(CF$_2$CClF)$_n$Cl, wherein n is in the range of 1 to 12.

The following examples are intended to further illustrate the various embodiments and advantages of the present invention without limiting it thereby. These examples illustrate the coupling of low molecular weight CTFE telomers to produce a coupled olefin which can then be reacted with a suitable fluorinating agent to produce a saturated product of higher molecular weight. Specifically, Example 1 illustrates the coupling of two telomers having a chain length of 1. Example 2 further illustrates the coupling of two telomers having a chain length of 1, while Example 6 illustrates the coupling of two telomers of chain lengths 1 and 2. Examples 3, 4 and 5, illustrate the fluorination of the coupled products of Example 2, with and without catalysts. Example 7 illustrates the fluorination of the coupled products of Example 6.

EXAMPLE 1

A 500 ml. 3-neck flask was provided with a mechanical stirrer, a condenser and a thermometer. The flask was charged with 213 grams of Cl$_3$CCF$_2$CFCl$_2$, 44 grams of iron powder, 2.0 grams of FeCl$_2$, and 150 ml. of CH$_3$CN. The entire apparatus was purged with N$_2$ and the reaction was carried out in an N$_2$ atmosphere at 80° C. On heating, a very vigorous and exothermic reaction took place. The heating was discontinued and the contents were cooled to maintain the desired reflux conditions. The contents of the flask were refluxed for 2½ hours. After filtration of the product and removal of the solvent, 138 grams of crude C$_6$F$_6$Cl$_6$ olefin was obtained. This compound was purified by distillation to give 126.5 grams of material (81% yield) having a boiling point of 45° C. at 0.15 mm Hg. with 98.5% purity (G.C.).

EXAMPLE 2

Using the conditions of Example 1, one liter (1750 gms.) of distilled $Cl_3CCF_2CFCl_2$ was added over a 6 hour period to a mixture of 358 gms. of iron powder in one liter of $CH_3CN$ under reflux conditions at a temperature ranging from 82° C. to 94° C. After workup, an 81% yield of distilled $C_6F_6Cl_6$ was obtained.

EXAMPLE 3

A sample of $C_6F_6Cl_6$ olefin prepared according to the coupling procedure of Example 2 was reacted with $ClF_3$ and 1% $FeCl_3$ as a catalyst at a temperature of 130° C. to saturate the olefin. The flow of $ClF_3$ was continued until the reaction product showed no unsaturation as determined by the $KMnO_4$ oxidation test*. The reaction product was then treated with moist $Na_2CO_3$, filtered and distilled. A sample of the treated reaction product was found to have a viscosity of 2.4 centistokes at a temperature of 38° C.

*The $KMnO_4$ oxidation test is a standardized technique for determining unsaturation of telomers of this type, and generally comprises adding 0.06 ml. of 1% aqueous $KMnO_4$ to a solution of 1 gram of telomer dissolved in 10 ml. of acetone. If the solution remains pink in color for at least 15 minutes, the telomer contains satisfactory limits of unsaturation.

EXAMPLE 4

Following the procedure of Example 2, a sample of $C_6F_6Cl_6$ olefin was reacted with $ClF_3$ and 1% $CoF_3$ as a catalyst at a temperature of 130° C. to saturate the olefin. The reaction product was treated with 1% moist $Na_2CO_3$, filtered and distilled.

EXAMPLE 5

Following the procedure of Example 3, a sample of $C_6F_6Cl_6$ olefin was reacted with $ClF_3$ without a catalyst at 130° C. until the reaction product passed the $KMnO_4$ oxidation test. The reaction product was treated with moist $Na_2CO_3$, filtered and distilled. A sample of the treated reaction product was found to have a viscosity of 2.9 centistokes at a temperature of 38° C.

EXAMPLE 6

To a refluxing mixture of 811 grams (3.0M) of $CCl_3CF_2CFCl_2$ and 1160 grams (3.0M) of $CCl_3(CF_2CClF)_2Cl$ in 1 liter of $CH_3CN$ was added 336 grams (6.0M) of iron powder. On work-up of the reaction mixture a 1337.5 grams (89% yield) of product was obtained having the following olefins present:

$Cl_2FCF_2CClC=CClCF_2CFCl_2$ $Cl_2FCF_2CClC=CCl(CF_2CFCl)_2Cl$ $Cl(CFClCF_2)_2ClC=CCl(CF_2CFCl)_2Cl$

EXAMPLE 7

A 401 gram sample containing a mixture of olefins produced by coupling a mixture of telomers (n=1, 2) as in Example 6 was saturated by passing $ClF_3$ through the mixture at a rate of 27 ml/minute (diluted with 15 ml/minute of $N_2$) at a temperature of 135° C. for 9½ hours. The temperature was then raised to about 200° C. and the $ClF_3$ passage was continued. After the sample passed the $KMnO_4$ test, it was stirred with moist soda ash and filtered.

While various embodiments and exemplifications of this invention have been shown and described in the specification, modifications and variations thereof will be readily appreciated by those skilled in the art. It is to be understood, therefore, that the appended claims are intended to cover all such modifications and variations which are considered to be within the scope and spirit of the present invention.

What is claimed is:

1. A process for coupling two saturated chlorotrifluoroethylene telomers, each telomer having the general formula $CCl_3(CF_2CFCl)_nCl$, where n is one or two, which comprises reacting said telomers in a solvent with a sufficient amount of iron to form a coupled olefin selected from the group consisting of $Cl_2FCF_2CClC=CClCF_2CFCl_2$, $Cl_2FCF_2CClC=CCl(CF_2CFCl)_2Cl$, and $Cl(CFCLCF_2)_2ClC=CCl(CF_2CFCl)_2Cl$, and mixtures thereof, wherein a small amount of $FeCl_2$ is added to the reaction mixture.

2. The process of claim 1 wherein one telomer has one repeating unit and the other telomer has two repeating units.

3. The process of claim 1 wherein the iron is present in powdered form.

4. The process of claim 3 wherein the iron is present in at least a stoichiometric amount based on the amount of telomer present.

5. The process of claim 1 wherein the reaction is conducted under reflux conditions.

6. The process of claim 1 wherein the reaction is conducted at a temperature of from about 50° C. to about 150° C. and at about atmospheric pressure.

7. The process of claim 1 wherein the solvent is acetonitrile.

* * * * *